US006004562A

United States Patent [19]

Campagnari

[11] Patent Number: 6,004,562

[45] **Date of Patent: *Dec. 21, 1999**

[54] **OUTER MEMBRANE PROTEIN B1 OF *MORAXELLA CATARRHALIS***

[75] Inventor: Anthony A. Campagnari, Hamburg, N.Y.

[73] Assignee: The Research Foundation of the State University of New York, Amherst, N.Y.

[ * ] Notice: This patent issued on a continued prosecution application filed under 37 CFR 1.53(d), and is subject to the twenty year patent term provisions of 35 U.S.C. 154(a)(2).

[21] Appl. No.: 08/698,652

[22] Filed: Aug. 16, 1996

[51] Int. Cl.[6] .......................... A61K 39/00; A61K 39/02

[52] U.S. Cl. .................................... 424/251.1; 424/184.1; 424/234.1

[58] Field of Search ............................ 424/234.1, 251.1, 424/184.1

[56] References Cited

FOREIGN PATENT DOCUMENTS 9303761 3/1993 WIPO .......................... A61K 39/095

OTHER PUBLICATIONS

Yu et al., "The interaction between human transferrin and transferrin binding protein 2 from Moraxella catarrhalis differs from that of other human pathogens", Microbial Pathogenesis, vol. 15, pp. 433–445, 1993.

Sethi, et al., "Serum Antibodies to Outer Membrane Proteins of Moraxella catarrhalis in Patients with Bronchiectasis: Identification of OMP B1 as an Important Antigen", Infection and Immunity, vol. 63, pp. 1516–1520, 1995.

Campagnari et al., "Growth of Moraxella catarrhalis with Human Transferrin and Lactoferrin: Expression of Iron–Repressible Proteins without Siderophare Production", Infection and Immunity, vol. 62, No. 11, pp. 4909–4914, 1994.

Murphy. Microbiological reviews 60(2): 267–279, 1993 (Jun.).

Campagnari et al. Infection and Immunity 62(11): 4909–4914, 1994.

Sethi et al. Infection and Immunity 63(4): 1516–1520, 1995.

Immunization Practices Advisory Committee, Clin. Phar. 8: 839–850, 1989.

Mackett et al. Human Vaccines and Vaccination, B10 S Scientific Publishers, Ltd., UK. 1995.

*Primary Examiner*—James C. Housel
*Assistant Examiner*—V. Ryan
*Attorney, Agent, or Firm*—Hodgson, Russ, Andrews, Woods & Goodyear, LLP

[57] ABSTRACT

An isolated and purified outer membrane protein B1, and peptides formed therefrom, of *Moraxella catarrhalis* are described. A method for the isolation and purification of outer membrane protein B1 from a bacterial strain that produces B1 protein, e.g. *Moraxella catarrhalis*, comprises growing the bacteria in culture in iron-depleted medium to enhance the expression of the B1 protein, harvesting the bacteria from the culture, extracting from the harvested bacteria a preparation substantially comprising an outer membrane protein preparation, contacting the outer membrane preparation with an affinity matrix containing immobilized transferrin wherein B1 protein binds to the transferrin, and eluting the bound B1 protein from the transferrin. Disclosed are the uses of the B1 protein as an immunogen for vaccine formulations, and as antigens in diagnostic immunoassays.

10 Claims, 2 Drawing Sheets

A
B
C
A
B
C
1
2

OUTER MEMBRANE PROTEIN B1 OF *MORAXELLA CATARRHALIS*

FIELD OF INVENTION

The present invention relates a protein associated with the outer membrane of *Moraxella catarrhalis*. More particularly, the invention is directed to methods for the isolation and purification of outer membrane protein B1 of *Moraxella catarrhalis*, isolated and purified B1 protein, compositions containing B1 protein, and uses thereof.

BACKGROUND OF THE INVENTION

*Moraxella catarrhalis* is an important human respiratory tract pathogen. *M. catarrhalis* is the third most common cause of otitis media in infants and children, after *Streptococcus pneumoniae* and nontypeable *Haemophilus influenzae*, as documented in studies in which tympanocentesis has been used to establish the etiologic agent (Murphy, 1989, *Pediatr. Infect: Dis. J.* 8:S75–S77). *M. catarrhalis* is a common cause of sinusitis and conjunctivitis in both children and adults (See for example, Bluestone, 1986, *Drugs* 31:S132–S141; Brorson et al., 1976, *Scand. J. Infect. Dis.* 8:151–155; and Romberger et al., 1987, *South. Med. J.* 80:926–928); and is an important cause of lower respiratory tract infections in adults with chronic bronchitis and chronic obstructive pulmonary disease (Murphy et al., 1992, *Am. Rev. Respir. Dis.* 146:1067–1083; Catlin, 1990, *Clin. Microbiol. Rev.* 3:293–320). Additionally, *M. catarrhalis* can cause pneumonia, endocarditis, septicemia, and meningitis in immunocomprised hosts (Cocchi et al., 1968, *Acta Paediatr. Scand.* 57:451–3; Douer et al., 1977, *Ann. Intern. Med.* 86:116–119; McNeely et al., 1976, *Am. Rev. Respir. Dis.* 114:399–402).

Since recurrent otitis media is associated with substantial morbidity, and the attendant health care costs, there is interest in developing strategies for identifying and preventing these infections. One such approach is the development of vaccines for preventing bacterial otitis media. Besides infants and children benefitting from a vaccine to prevent otitis media caused by *M. catarrhalis*, adults with chronic obstructive pulmonary disease, and immunocompromised children and adults would benefit from a vaccine to prevent infections caused by *M. catarrhalis*. Outer membrane proteins are being investigated as antigens having utility in diagnosing and vaccinating against disease caused by bacterial pathogens, such as *M. catarrhalis*.

In an original typing scheme, eight major outer membrane proteins, designated by the letters A–H, were identified (Murphy et al., 1989, *Microbial Pathogen.* 6:159–174; Bartos et al., 1988, *J. Infect. Dis.* 158: 761–765). Further characterization of the outer membrane proteins of *M. catarrhalis* have added to this typing scheme. A protein having an apparent molecular mass of approximately 80 to 81 kilodaltons (kDa), as determined by sodium dodecyl polyacrylamide gel electrophoresis (SDS-PAGE), has been described previously ("CopB protein": Helminen et al., 1993, *J. Inf. Dis.* 168:1194–201; "OMP B2 protein": Sethi et al., 1995, *Infect. Immun.,* 63:1516–1520). CopB protein has been characterized as a surface-exposed, antigenically conserved protein that is a target for antibodies that enhance pulmonary clearance of *M. catarrhalis* in an experimental model of infection (Helminen et al., 1993, *Infect. Immun.* 61:2003–2010). Further, CopB may be involved in the serum resistance of *M. catarrhalis* in an infected host (Helminen et al., 1993, *J. Inf. Dis.* 168:1194–201).

Another outer membrane protein has recently been described. B1 protein was shown to be expressed in detectable amounts in the outer membrane of *M. catarrhalis* under iron-limiting conditions, i.e., expressed when the organism is growing in an iron-limited environment (Campagnari et al., 1994, *Infect. Immun.* 62:4909–4914). However, when the organism is grown in an iron-rich environment, the expression of the B1 protein becomes repressed. The B1 protein, having an apparent molecular mass of approximately 81 to 84 kilodaltons (kDa) as determined by SDS-PAGE, has been demonstrated to be distinct from the CopB (OMP B2) protein by differences in migration pattern in polyacrylamide gels, by antibody reactivity, and by expression in iron-limiting conditions (Campagnari et al., 1994, supra; and Campagnari et al., September 1996, pending in *Infect. Immun.*). Additional studies show that OMP B1 contains epitopes exposed at the surface of the bacterium expressing it, and that these surface-exposed epitopes are important antigens for the human humoral response to *M. catarrhalis* infection (see, e.g., Example 3 herein).

Properties of the B1 protein indicate that the protein has utility in the diagnosis of and vaccination against diseases caused by bacterial pathogens, such as *M. catarrhalis*, that produce B1 protein or surface-exposed epitopes cross-reactive with B1 protein epitopes. Thus, it would be advantageous to provide a method for the purification of B1 protein; and purified B1 protein for use as an antigen in the generation of diagnostic reagents, and for immunogenic preparations such as vaccines.

SUMMARY OF THE INVENTION

In accordance with one object of the present invention, there is provided a method for the isolation and purification of outer membrane protein B1 from a bacterial strain that produces B1 protein, e.g. *Moraxella catarrhalis*. The method relates to the unexpected finding that the B1 protein binds transferrin. The method comprises growing the bacteria in culture in iron-depleted medium to enhance the expression of the B1 protein, harvesting the bacteria from the culture, extracting from the harvested bacteria a preparation substantially comprising an outer membrane protein preparation, contacting the outer membrane preparation with an affinity matrix containing immobilized affinity molecules having binding specificity with the B1 protein, wherein B1 protein and the affinity molecules bind, and eluting the bound B1 protein from the affinity molecules.

In another object of the present invention, there is provided an isolated and purified B1 protein. The isolated and purified B1 protein is substantially free from other outer membrane proteins and components (e.g., lipooligosaccharide (LOS)) using the method according to the present invention. Further, denaturing conditions are not used in the purification process. Thus, the immunogenicity of the isolated and purified B1 protein may be well preserved. The isolated and purified B1 protein of the present invention may be used as immunogens in prophylactic and/or therapeutic vaccine formulations; or as an antigen in diagnostic immunoassays directed to detection of *M. catarrhalis* infection by measuring an increase in serum titer of *M. catarrhalis*-specific antibody in acute phase and/or convalescent sera. Also, B1 protein may be used to generate B1-specific antibody which may be useful for passive immunization, and as reagents for diagnostic assays directed to detecting the presence of *M. catarrhalis* in clinical specimens.

These objects and further features and advantages of the invention will be better understood from the description of the preferred embodiments when considered in relation to the figures in which:

DETAILED DESCRIPTION OF THE INVENTION

Definitions

Figures 1A, 1B:
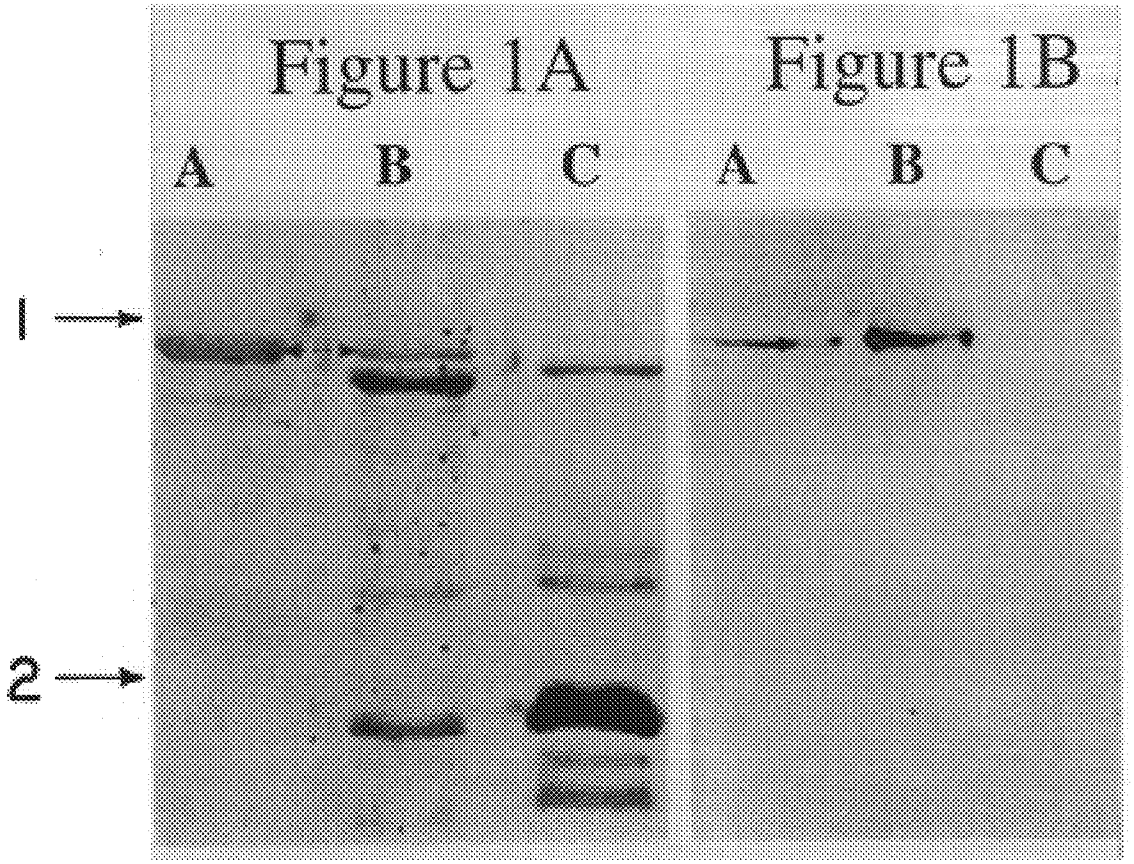
FIG. 1A is a digital image created by scanning a stained polyacrylamide gel, wherein lane A represents 15 μg of B1 protein purified from an affinity matrix column containing immobilized human transferrin. Arrows 1 and 2 represent molecular mass markers 85 kDa and 50 kDA, respectively.
FIG. 1B is a digital image created by scanning a Western blot, wherein lane A represents 15 μg of OMP B1 purified from the affinity matrix column containing the immobilized human transferrin; lane B containing 15 μg of outer membrane proteins prepared from *M. catarrhalis* grown in iron-limited conditions; and lane C containing 15 μg of outer membrane proteins prepared from *M. catarrhalis* grown in iron-replete conditions.

By the terms "OMP B1", and "B1 protein" are meant, for the purposes of the specification and claims, to refer to a protein having the following distinguishing and functional characteristics:

(a) the protein is substantially expressed by a bacterial strain that produces B1 protein, e.g., *M. catarrhalis*, and is detectable in the outer membrane of the bacterial strain, under iron-limiting conditions, i.e., when the organism is growing in an iron-limited environment;

(b) expression of the protein appears to become repressed when the bacterial strain is grown in an iron-rich environment;

(c) the protein has an apparent molecular mass of approximately 81 to 84 kDa as determined by SDS-PAGE;

(d) the protein, in its native conformation in the outer membrane, contains surface-exposed epitopes; and (e) the protein binds human transferrin, particularly iron-saturated transferrin.

Additionally, in the N-terminal portion of the amino acid sequence of the protein may be the nine amino acids in sequence LeuGlnGlyGlyPheTyrGlyProLys (SEQ ID NO:1). A peptide with this sequence may be synthesized using any of the methods known to those skilled in the art for synthesizing peptides.

By the terms "isolated and purified" and "substantially free from other outer membrane proteins and components" is meant, for the purposes of the specification and claims, to refer to a B1 protein preparation that appears to be at least approximately 80% pure, and may be up to approximately 99% pure, as, for example, determined by SDS-PAGE.

By the term "individual" is meant, for the purposes of the specification and claims to refer to any mammal, especially humans.

By the term "iron-repressible proteins" is meant, for the purposes of the specification and claims to refer to outer membrane proteins which are expressed in detectable amounts when *M. catarrhalis* is grown in iron-depleted or iron-limiting conditions, but which detectable expression is repressed by placing the iron-starved bacteria into an iron-replete environment. An iron-limited condition is illustrated by growing the bacteria in chemically defined medium which has been treated with an iron chelator, as described in an illustration with more detail below. An iron-replete condition is illustrated by growing the organisms in any one of several standard growth media known to those skilled in the art for growing *M. catarrhalis*, such as brain heart infusion broth.

By the term "immunoreactive" is meant, for the purposes of the specification and claims to refer to binding specificity between an antigen (e.g., OMP B1) and antibody (e.g., anti-OMP B1 antibody).

By the term "affinity molecule" is meant, for the purposes of the specification and claims to refer to a molecule having binding affinity and specificity with OMP B1. More particularly, demonstrated herein is the binding affinity and specificity of OMP B1 for transferrin, particularly iron-saturated transferrin. Also demonstrated herein, is the binding affinity and specificity of monoclonal antibodies for OMP B1.

Proteins and peptides are chemical compositions made up of a sequence of amino acid units. By the term "consisting essentially" is meant as a term, with an accepted meaning in the chemical patent practice and for the purposes of the specification and claims, to refer to the inclusion of unspecified amino acids (deletion/addition/substitution) which do not materially affect the basic and novel characteristics of the composition; i.e. conservative substitution or modification of one or more amino acids in that sequence such that the tertiary configuration of the protein or peptide is substantially unchanged. "Conservative substitutions" is defined by aforementioned function, and includes substitutions of amino acids having substantially the same charge, size, hydrophilicity, and/or aromaticity as the amino acid replaced Such substitutions, known to those of ordinary skill in the art, include glycine-alanine-valine; isoleucine-leucine; tryptophan-tyrosine; aspartic acid-glutamic acid; arginine-lysine; asparagine-glutamine; and serine-threonine. "Modification", in relation to amino acid sequence of a protein or peptide, is defined functionally as a deletion of one or more amino acids which does not impart a change in the conformation, and hence the biological activity, of the protein or peptide sequence.

The present invention is directed to a bacterial outer membrane protein of *M. catarrhalis* wherein the protein has been designated "B1". One role of this protein-to the growth and survival of *M. catarrhalis* relies on the binding specificities of the B1 protein. It is well established that iron is a critical element which is essential for the growth of many different microbial pathogens. Most of the iron present in the human body is intracellular in the ferrous form as hemoglobin, heme, ferritin, and hemosiderin. Most extracellular iron is complexed to the high affinity iron-binding glycoproteins transferrin and lactoferrin. Thus, with the virtual absence of free iron available in the body because of the presence of various iron-binding compounds, many microbial pathogens in humans have had to develop highly specific mechanisms by which to obtain the necessary iron for survival in vivo. These mechanisms include, but are not limited to the production of hemolysins to free intracellular iron from heme and hemoglobin; the secretion of siderophores, high affinity iron chelators which compete for iron in the microenvironment and which are then internalized by the microbial pathogen; and the expression of specific OMPs in response to iron limitation, wherein the OMPs having affinity for iron-binding compounds.

The unexpected finding that the B1 protein binds iron-saturated transferrin provides a method by which B1 protein may be isolated and purified from a bacterial strain that produces B1 protein, e.g. *Moraxella catarrhalis*. The preferred method comprises growing the bacteria in culture in iron-depleted medium to enhance the expression of the B1 protein, harvesting the bacteria from the culture, extracting from the harvested bacteria a preparation substantially comprising the outer membrane proteins of the bacteria, contacting the outer membrane preparation with an affinity matrix containing immobilized, iron-saturated transferrin wherein B1 protein binds to the transferrin, and eluting the bound B1 protein from the transferrin. Alternatively, one or more monoclonal antibodies having binding affinity and specificity may be used, in place of or in conjunction with, transferrin as the affinity molecules immobilized to the affinity matrix Further, the unexpected finding that the B1 protein binds iron-saturated transferrin provides evidence that the B1 protein is involved in one of the mechanisms by which *M. catarrhalis* obtains iron from the iron-binding compound human transferrin. It has recently been demonstrated that *M. catarrhalis* can utilize human transferrin as the sole source of iron for in vitro growth (Campagnari et al., 1994, *Infect. Immun.* 62:4909–4914, herein incorporated by reference). Because B1 protein appears to play an important role for *M. catarrhalis* survival in vivo, this finding is one factor in considering B1 protein as an immunogen in a vaccine against disease caused by *M. catarrhalis*. For example, OMPs that function as transferrin-binding proteins, have been demonstrated to be important in the pathogenesis of infections caused by pathogenic bacteria *Neisseria meningitidis* and *N. gonorrhoeae* (Criado et al., 1993, *Res. Microbiol.* 144:77–82; Litwin et al., 1993, *Clin. Microbiol. Rev.* 6:137–149). Thus isolated and purified B1 protein, or peptides made by enzymatically cleaving B1 protein, may be used as immunogens in various vaccine formulations in the prevention of otitis media, sinusitis, conjunctivitis, and lower respiratory tract infections caused by *M. catarrhalis*. Additionally, according to the present invention, the B1 protein, and peptides derived therefrom, may be used to generate *M. catarrhalis*-specific antisera useful for passive immunization against infections caused by *M. catarrhalis*. Isolated and purified B1 protein, or peptides derived therefrom, may also be used as an antigen for diagnostic immunoassays or for generating *M. catarrhalis*-specific antisera of diagnostic value.

For purposes of the description, the methods and compounds of the present invention will be illustrated in the following examples.

EXAMPLE 1

This Example illustrates the ability of OMP B1 to bind human transferrin. Additionally, this Example illustrates the isolation and purification of B1 protein by utilizing its ability to bind human transferrin.

The identification of an OMP that binds to iron-saturated human transferrin was characterized by growing *M. catarrhalis* in culture in an iron-depleted medium to enhance the expression of iron-repressible proteins, harvesting the bacteria from the culture, extracting from the harvested bacteria a preparation substantially comprising the bacterial outer membrane proteins, contacting the outer membrane preparation with an affinity matrix containing immobilized transferrin wherein protein(s) present in the outer membrane protein preparation that have transferrin-binding specificity will bind to the transferrin, and eluting the bound protein(s) from the transferrin.

To grow *M. catarrhalis* in iron-limiting conditions, an iron-depleted, defined growth medium was used. The defined medium is described previously by Morse et al. (1980, *Can. J. Microbiol.* 26:13–20, hereinafter incorporated by reference). The defined medium was iron depleted by treatment with an iron-chelator (Chelex-100) and prepared as previously described (West et al., 1985, *Infect. Immune* 47:388–394, herein incorporated by reference). This chelator-treated, defined medium is called "CDM 0". *M. catarrhalis* was inoculated onto CDM 0 agar plates and grown in a 5% $CO_2$ atmosphere at 37° C. overnight. Organisms from these plates were used to inoculate CDM 0 broth cultures, and the flasks were placed in a water bath shaker at 37° C. with constant agitation.

A preparation enriched in outer membrane proteins was prepared by a previously described method (Bartos et al., 1988, *Infect. Dis.* 158:761–765, herein incorporated by reference). Briefly, the bacteria were harvested from the CDM 0 broth cultures by centrifugation at 1,500×g for 10 minutes at 4° C. The wet weight of the harvested bacteria was determined, and the bacteria were then suspended in 1 ml of 1M $NaC_2H_3O_2$ with 0.001 M beta-mercaptoethanol (pH 4.0) per gram of bacterial cells. All buffers used in the purification and isolation procedure contained protease inhibitors (e.g., a serine protease inhibitor, and a broad-spectrum protease inhibitor, added according to the manufacturer's instructions). Freshly prepared zwitterionic detergent (5% Zwittergent 3–14) containing 0–5 M $CaCl_2$, pH 8.0, was added, and the suspension was vortexed. Cold ethanol was added to the supernatant to a final volume of 20%, and the mixture was centrifuged at 17,000×g for 10 minutes at 40C. The pellet was discarded, cold ethanol was added to a final volume of 80%, and the centrifugation step was repeated for 20 minutes. The pellets, substantially comprising outer membrane proteins, were air dried and resuspended in a detergent buffer (0.005% Zwittergent, 0.05 M Tris, 0.01 M EDTA, pH 8.0). There are other methods known to those skilled in the art for isolating bacterial outer membranes from *M. catarrhalis*, such as by EDTA-heat-induced vesicles (Sethi et al., 1995, *Infect. Immun.* 63:1516–1520; herein incorporated by reference).

Commercially available human transferrin (apotransferrin) was saturated with iron using ferric citrate as previously described (West et al., 1985, supra). Briefly, the transferrin was incubated with a ferric nitrate/sodium citrate solution for 1 hour at 37° C. This mixture was then dialyzed overnight in a buffer containing Tris, sodium chloride, and bicarbonate Percent of iron saturation of the transferrin was determined using a previously described method (Adams et al., 1990; *Infect. Immun.* 58:2715–2718). An affinity column was prepared by coupling the iron-saturated human transferrin, as the affinity molecules, to a cyanogen bromide (CNBr)-activated matrix resin (Sepharose 6B) in accordance with the manufacturer's instructions. Briefly, 1 g of CNBr-activated matrix resin was preswollen with buffer and mixed with 5 mg of human transferrin that was 92% saturated with iron. Any activated sites on the column matrix that did not bind the transferrin were then blocked with the addition of 1 M ethanolamine. This matrix was then extensively washed with coupling buffer comprising 0.1 M $NaHCO_3$ with 0.5 NaCl, pH 8.3 until the optical density at 280 nm of the wash buffer was below 0.05.

To identify if any OMPs, from *M. catarrhalis* grown in iron-limiting conditions (CDM 0), would bind to iron-saturated human transferrin, the OMP preparation was run over the affinity matrix column containing immobilized transferrin. Approximately 500 μg of the OMP preparation was incubated with a 3 ml portion of the affinity matrix containing immobilized transferrin for 24 hours at 25° C. The mixture was packed into a column, and the column was washed with a detergent buffer (50 mM Tris, 1 M NaCl, 5 mM EDTA, pH 8.3, 0.5% sarcosyl), and washed finally with a Tris buffer (50 mM Tris, 1 M NaCl, pH 8.3). All washes were monitored by taking samples, and analyzing the samples by SDS-PAGE. After the washing step, any OMP(s) remaining bound to the immobilized transferrin were eluted from the affinity column with 0.2 M glycine, pH 2.8. The fractions were collected into 0.1 M Tris buffer, pH 9, which adjusted the final pH to approximately 7. All fractions with an optical density at 280 nm of ≧0.1 were pooled and dialyzed against phosphate-buffered saline. The resultant product was concentrated and washed with distilled water by centrifugation.

As shown in FIG. 1A, the final product was analyzed by SDS-PAGE. FIG. 1A is a digital image created by scanning a stained polyacrylamide gel. Lane A represents 15 μg of the product eluted from the affinity matrix column containing the immobilized human transferrin. Shown is a single band of apparent molecular mass of approximately 81–84 kDa. Arrows 1 and 2 represent molecular mass markers 85 kDa and 50 kDA, respectively. Thus, the transferrin-binding protein isolated from the outer membrane of *M. catarrhalis* grown in iron-limited conditions migrates at the same apparent molecular mass to that of OMP B1. Monoclonal antibody studies, described below, confirm the identity of this human transferrin binding protein as OMP B1. B1 protein also binds to transferrin without iron (apotransferrin) but with less affinity and/or avidity than compared with the binding to iron-saturated transferrin.

Thus, a method for isolating and purifying OMP B1 from a bacteria expressing OMP B1 comprises growing the bacteria in culture in an iron-depleted medium to enhance the expression of iron-repressible proteins; harvesting the bacteria from the culture; extracting from the harvested bacteria a preparation substantially comprising the bacterial outer membrane proteins; contacting the outer membrane preparation with an affinity matrix containing affinity molecules comprising immobilized transferrin (preferably iron-saturated transferrin), wherein B1 protein having transferrin-binding specificity will bind to the transferrin; and eluting the bound B1 protein from the transferrin. This method may be used for isolating and purifying B1 protein from *M. catarrhalis*, or a recombinant organism (such as *Escherichia coli*) genetically engineered to express B1 protein. As an alternative method, and using similar method steps as described above for making and using an affinity matrix containing transferrin as the immobilized affinity molecules, one or more monoclonal antibodies to B1 protein may be used as either the sole immobilized affinity molecules, or in combination with transferrin as immobilized affinity molecules, for isolating and purifying B1 protein. Illustrative examples how to make such monoclonal antibodies, and illustrative monoclonal antibodies 7B3 and 1F11, are described below.

Amino acid analysis of the isolated and purified B1 protein resulted in the identification of a sequence near the N-terminal portion of the protein, wherein the sequence consists of nine amino acids in sequence: LeuGlnGlyGlyPheTyrGlyProLys (SEQ ID NO:1). A peptide with this sequence may be synthesized using any one of the several methods known to those skilled in the art for synthesizing peptides.

EXAMPLE 2

This Example illustrates the generation of a monoclonal antibody (MAb) to OMP B1.

There is believed to be no published studies on the development of monoclonal antibodies to iron-regulated proteins of *M. catarrhalis*. Thus, one objective was to develop a series of monoclonal antibodies to different epitopes of OMP B1 for characterizing antigenic conservation amongst strains of *M. catarrhalis*, and to detect surface-exposed epitopes. Monoclonal antibodies to OMP B1 were developed using a modification of a previously described protocol (Haase et al., 1991, *Infect. Immun.* 59:1278–1284). BALB/C mice were immunized (day 1) and given a booster dose (day 28) by intraperitoneal injection with $10^5$ colony forming units of viable *M. catarrhalis* strain 25240 grown in CDM 0 which express iron-repressible proteins. Hybridomas were initially screened by immunodot assay containing samples of outer membrane proteins prepared from *M. catarrhalis* strain 25240 grown in CDM 0. Positive clones by immunodot assay were further analyzed by SDS-PAGE and Western blot analysis. Two monoclonal antibodies, termed MAb 7B3 and MAb 1F11, were found to be specific for OMP B1. Such specificity was determined by Western blot analysis in which MAb 7B3 and MAb 1F11 were each found to react with a protein of an apparent molecular size in the range of approximately 81–84 kDa in outer membrane proteins prepared from *M. catarrhalis* grown in iron-limited conditions, and wherein no reactivity was observed with outer membrane proteins prepared from *M. catarrhalis* grown in iron-repleted conditions. Further, a Western blot was performed with both Mab 2.9F, a monoclonal antibody to OMP B2 (Sethi et al., 1995, supra), and MAb 7B3, the results of which confirm that MAb 7B3 is specific for OMP B1.

A method for making monoclonal antibodies immunoreactive with B1 protein involves the use of isolated and purified OMP B1 as the immunogen or an outer membrane preparation isolated from *M. catarrhalis* grown in iron-limited conditions, as an alternative to immunizing with viable *M. catarrhalis* grown in iron-limited conditions which express iron-repressible proteins. In either case, the immunogen is used to immunize an animal (such as BALB/c mice) at timed intervals. A few days following the last immunization, spleens from the immunized animal are harvested aseptically, and placed into a tissue culture dish containing tissue culture medium. The primed spleen cells containing B-lymphocytes are mixed with a immunoglobulin non-secreting plasmacytoma cell line (usually a 10:1 to 1:1 ratio) for fusion. Fusion can be accomplished by methods including contacting the cells with a fusion agent such as polyethylene glycol (1 ml of a 50% solution, MW 1400) or by electrofusion. The cells from the fusion are then cloned out in microtiter plate wells. Typically, the plasmacytoma cell line is deficient in an enzyme such as hypoxanthine guanine phosphoribosyl transferase such that fused hybridomas can be selected for by using a tissue culture selection medium such as a medium containing hypoxanthine, aminopterin, and thymidine. The hybridoma cultures are then incubated for several days, under standard tissue culture conditions, before the supernatants are tested for immunoreactivity to isolated and purified B1 protein and/or to OMP B1 present in an outer membrane preparation from *M. catarrhalis* grown in iron-limited conditions.

Both MAb 7B3 and MAb 1F11 react with OMP B1 isolated and purified according to the method of the present invention. Illustrated in FIG. 1B, a digital image created by scanning a Western blot, are lane A representing 15 μg of OMP B1 as isolated and purified from the affinity matrix column containing the immobilized human transferrin; lane B containing 15 μg of outer membrane proteins prepared from *M. catarrhalis* grown in iron-limited conditions; and lane C containing 15 μg of outer membrane proteins prepared from *M. catarrhalis* grown in iron-replete conditions. MAb 7B3 was reacted with the Western blot followed by developed with anti-mouse immunoglobulin M conjugated to horseradish peroxidase with subsequent substrate addition. Shown in both lanes A and B is a single band of apparent molecular mass of approximately 81–84 kDa, corresponding to B1 protein.

A competitive enzyme-linked immunosorbent assay (ELISA) was performed to determine if MAb 7B3 and MAb 1F11 react to the same epitope of OMP B1. Briefly, MAb 7B3 was used to coat an ELISA plate. Isolated and purified B1 protein, which had been biotinylated using methods known to those skilled in the art, was added to a first set of wells. Biotinylated B1 protein was added to a second series of wells, after pre-incubation with concentrations of MAb 1F11 ranging in concentrations from 10 μgs to 320 μgs as the inhibitor. The detection system involved the addition of streptavidin conjugated to peroxidase with subsequent substrate addition. Preincubating B1 protein with MAb 1F11 did not inhibit the ability of MAb 7B3 to bind to B1 protein, evidence that MAb 7B3 and MAb 1F11 are directed to different epitopes on B1 protein.

EXAMPLE 3

This Example illustrates properties of OMP B1 which support the use of B1 protein as an immunogen in a vaccine against disease caused by *M. catarrhalis*, or as an antigen for use in diagnostic assays.

For the B1 protein to be useful as an immunogen in a vaccine against disease caused by *M. catarrhalis*, or as an antigen for use in diagnostic assays, it must be antigenically conserved amongst strains of *M. catarrhalis*. Further, for the B1 protein to be useful as an immunogen in a vaccine, or as an antigen for use in diagnostic assays, it must be able to elicit an immune response in individuals, such as children and adults. Additionally, for utility as a vaccine immunogen, OMP B1 must have surface-exposed epitopes.

3.1 Antigenic conservation amongst strain

To determine the degree of antigenic conservation of OMP B1 among strains of *M. catarrahlis*, outer membrane proteins prepared from multiple clinical isolates of *M. catarrhalis* grown in iron-limited conditions were analyzed by Western blot analysis. Five isolates recovered from diverse clinical and geographic sources were analyzed, including strains isolated from the nasopharynx (strain 556) and middle ear fluids (strains 7169 and 035E) of children with otitis media, and strains isolated from the sputum (strains 48 and M10) of adults with chronic bronchitis. The Western blot containing the OMP preparations from the various strains were incubated with MAb 7B3 and developed with anti-mouse immunoglobulin M conjugated to horseradish peroxidase. The results showed that the OMP B1 epitope recognized by MAb 7B3 is expressed by each strain tested. Sixteen additional clinical isolates of *M. catarrhalis* were tested for reactivity with MAb 7B3, with all 16 isolates being immunoreactive. This additional evidence demonstrates that OMP B1 is antigenically conserved amongst clinical isolates.

A similar assay was performed using MAb 1F11. The same strains of *M. catarrhalis* that were tested for immunoreactivity with MAb 7B3 were also tested for immunoreactivity with MAb 1F11. Outer membrane proteins were prepared from the different clinical isolates grown in iron-limited conditions. Additionally, outer membrane proteins were prepared from a strain each of *N. meningitidis, N. gonorrhoeae*, and *Haemophilus influenzae*, grown in iron-limited conditions. The results demonstrated that MAb 1F11 reacts to an epitope conserved on OMP B1 expressed by all clinical isolates of *M. catarrhalis* tested, but importantly was not immunoreactive with outer membrane proteins prepared from other gram negative pathogens included in this study. This suggests that OMP B1 expresses one or more epitopes specific for *M. catarrhalis*.

3.2 Surface-exposed epitopes

For a bacterial protein, or peptide derived therefrom, to be useful as an antigen in vaccine formulations against infection caused by *M. catarrhalis*, one or more epitopes of OMP B1 must be surface-exposed. One method of assaying for surface exposure is by flow cytometry (Srikumar et al., 1992, *Mol. Microbiology* 6:665–676, herein incorporated by reference). Flow cytometry studies were performed with MAb 1F11 and iron-stressed, viable *M. catarrhalis* strain 25240. MAb 1F11, an IgG2b isotype, was affinity purified and then labeled with anti-mouse IgG coupled to fluorescein isothiocyanate (FITC) using methods known to those skilled in the art. An irrelevant antibody was used as a negative control antibody, and MAb 4G5, reactive to a surface epitope of LOS, was used as a positive control antibody. The results demonstrate that MAb 1F11 is an antibody that reacts to a surface-exposed epitope of OMP B1 expressed by *M. catarrhalis* grown in iron-limiting conditions.

3.3 Analysis of the human immune response to OMP B1

Because it is well known that human blood and body fluids present a naturally occurring iron-limited environment, it was suspected that *M. catarrhalis* may express OMP B1 in vivo. Studies were performed to detect if *M. catarrhalis* expresses OMP B1 in vivo, and whether OMP B1 is a target of the humoral response in individuals infected with *M. catarrhalis*. Sera was prepared from three children previously infected with different strains of *M. catarrhalis*. B1 protein, isolated and purified according to the method of the present invention, was added (10 μg per lane) to lanes of a polyacrylamide gel and SDS-PAGE and Western blots were performed. One section of the Western blot was reacted with MAb 7B3, followed by development with anti-mouse immunoglobulin M conjugated to horseradish peroxidase and subsequent substrate addition as a positive control. Other sections were each individually reacted with either of the convalescent serum from the three children previously infected with *M. catarrhalis*. The latter three sections were developed with protein A peroxidase and subsequent substrate addition. The results show that each child has serum IgG antibodies immunoreactive to OMP B1 isolated and purified according to the method of the present invention. These data are evidence that OMP B1 is expressed in vivo by *M. catarrhalis* and that the OMP B1 expressed is immunogenic in children. Additionally, it is noted that the OMP B1 used in this assay was purified from *M. catarrhalis* strain 25240. The strains infecting the children in this study were other than strain 25240. This is additional evidence that OMP B1 contains one or more conserved or cross-reactive epitopes which are immunogenic.

To confirm whether the immune sera reacted with surface-exposed epitopes, the serum from one of the three children previously infected with *M. catarrhalis* was used in an immunoabsorption assay. In this experiment, $10^6$ colony forming units of *M. catarrhalis* grown in iron-limited conditions, and of *M. catarrhalis* grown in iron-replete conditions, were incubated with separate aliquots of the serum for 4 hours. The bacteria were then removed, and each aliquot was diluted 1/100 and used to probe duplicate Western blots. Each Western blot contained 40 μg of isolated strain 25240 OMP B1 in lane a, and 10 μgs of OMPs from iron-stressed and iron-replete strain 25240 in lanes b and c, respectively. The data showed that preincubation of the serum with *M. catarrhalis* grown in iron-replete conditions did not affect immunoreactivity of the serum with OMP B1. In contrast, preincubation of the serum with *M. catarrhalis* grown in iron-limited conditions markedly reduced immunoreactivity of the serum with OMP B1. The results indicate that individuals infected with *M. catarrhalis* develop antibodies to surface-exposed epitopes of OMP B1.

Figure 2:
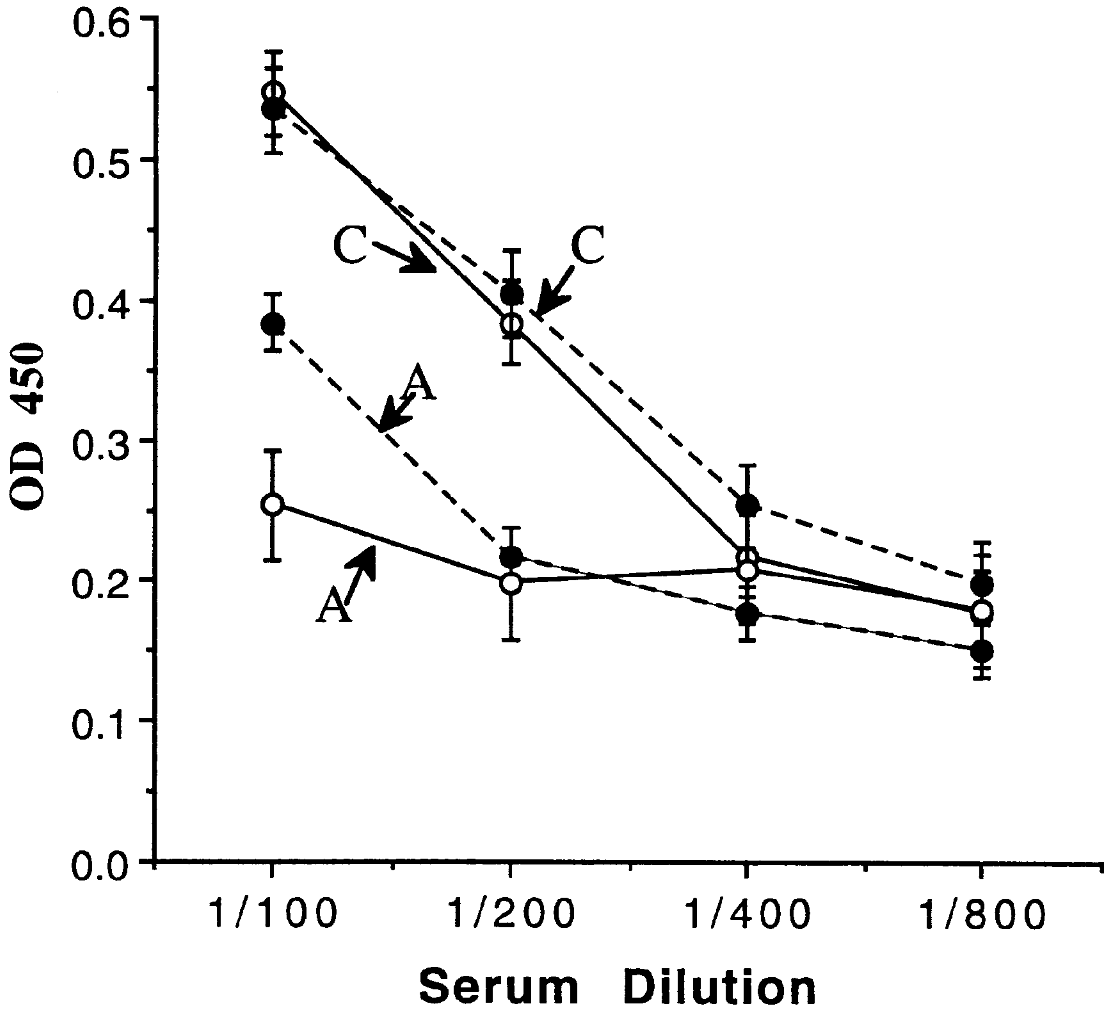
FIG. 2, is a graph showing levels of antibodies to OMP B1 in convalescent sera (C) and acute sera (A) from child 1 (dashed line) and child 2 (solid line).

To further evaluate the immune response of patients to this iron-regulated protein, acute and convalescent serum from 2 children infected with different strains of *M. catarrhalis* were analyzed for antibodies immunoreactive with OMP B1 isolated from strain 25240 using the methods according to the present invention. Briefly, purified OMP B1 was used to coat the wells of an ELISA plate. Dilutions of the acute sera and convalescent sera (1/100, 1/200, 1/400, and 1/800) were incubated with the purified OMP B1 contained within the respective wells. The ELISAs were developed using protein A peroxidase with subsequent substrate addition. The results, summarized in FIG. 2, show that the convalescent sera (C) from child 1 (dashed line) and child 2 (solid line) had increased levels of antibodies to OMP B1 compared to their respective acute sera (A). These findings are further evidence that (a) OMP B1 is expressed in vivo and that OMP B1 is immunogenic in infected individuals; and (b) that OMP B1 contains one or more conserved or cross-reactive epitopes amongst clinical isolates. Further, it is evident from the data that the titer of antibody increases with the progression of the *M. catarrhalis* infection, suggesting that antibodies to OMP B1 are important antigens in the humoral immune response to *M. catarrhalis*. Additionally, this embodiment confirms the utility of purified B1 protein as an antigen in diagnostic assays for the detection of antibodies against OMP B1 in individuals infected with *M. catarrhalis.*

EXAMPLE 4

This Example illustrates the use of B1 protein or antibodies to B1 protein for use in diagnostic assays to detect infection caused by *M. catarrhalis.*

B1 protein, isolated according to the method of the present invention, or peptides formed therefrom using methods and proteolytic enzymes (e.g. trypsin, chymotrypsin) or chemical reagents (e.g. CNBr) known to those skilled in the art for generating peptides from proteins, can be used as an antigen for diagnostic assays. Alternatively, B1 protein, or peptides formed therefrom, can be used as immunogens for generating *M. catarrhalis*-specific antisera of diagnostic value. Antigenic sites of a protein may vary in size but can consist of from about 7 to about 14 amino acids. Thus, a protein the size of OMP B1 may contain many discrete antigenic epitopes (as evidenced by differential reactivity with MAb 7B3 and MAb 1F11). Consequently, using either enzymatic or chemical digestion of B1 protein, or synthetic processes, peptides of at least 7 to 14 amino acids in size may be generated which contain antigenic epitopes of OMP B1. Immunopurification of the peptides formed from B1 protein may be accomplished using methods known in the art for immunoaffinity chromatography, such as using either or both MAb 7B3 and MAb 1F11 as the immobilized affinity reagent. Other purification techniques known to those skilled in the art include molecular-sieve chromatography, and ion-exchange chromatography.

Alternatively, the peptides can be synthesized from the amino acid sequence of the B1 protein using one of the several methods of peptide synthesis known in the art including standard solid peptide synthesis using tert-butyloxycarbonyl amino acids (Mitchell et al., 1978, *J. Org. Chem.* 43:2845–2852), using 9-fluorenylmethyloxycarbonyl amino acids on a polyamide support (Dryland et al., 1986, *J. Chem. So. Perkin Trans. I,* 125–137); by pepscan synthesis (Geysen et al., 1987, *J. Immunol. Methods* 03:259; 1984, *Proc. Natl. Acad. Sci. USA* 81:3998); or by standard liquid phase peptide synthesis. Modification of the peptides, such as by deletion and substitution of amino acids (and including extensions and additions to amino acids) and in other ways, may be made so as to not substantially detract from the immunological properties of the peptide. In particular, the amino acid sequence of the peptide may be altered by replacing one or more amino acids with functionally equivalent amino acids resulting in an alteration which is silent in terms of an observed differences in the physicochemical behavior and specificity of the peptide.

In one embodiment, purified B1 protein, or peptides formed therefrom, may be used as antigens in immunoassays for the detection of *M. catarrhalis*-specific antisera present in the body fluid of an individual suspected of having an infection caused by *M. catarrhalis* (see, e.g., Example 3, herein). The body fluids include, but are not limited to, middle ear fluid, sputum, blood, and fluids from the nasopharynx, eye, and adenoid. A diagnostic assay utilizing as an antigen B1 protein or a peptide formed therefrom, includes any immunoassay known in the art including, but not limited to, radioimmunoassay, ELISA, "sandwich" assay, precipitin reaction, agglutination assay, fluorescent immunoassay, and chemiluminescence-based immunoassay. Thus, for example, B1 protein or a peptide formed therefrom may be used as an antigen in an ELISA in which the antigen is immobilized to a selected surface; followed by blocking of unbound areas of the surface; contacting the clinical sample with the selected surface containing immobilized antigen; washing the surface to remove materials in the clinical sample which are not bound to the antigen; and detection of any immune complexes present (e.g., antibody to B1 protein complexed to B1 protein) with a detectable moiety, such as by adding protein A peroxidase with subsequent color development. Other detectable moieties, conjugates and/or substrates known to those skilled in the art of diagnostics may be used to detect immunocomplexes formed. Thus, a diagnostic kit would contain the isolated B1 protein, or peptide formed therefrom as the antigen; a means for facilitating contact between the clinical sample and the antigen (e.g., for an ELISA, a microtiter plate or wells); and a means for detecting the presence of immunocomplexes formed.

In another embodiment of the invention, using methods known to those skilled in the art, B1 protein or a peptide formed therefrom may be used as an immunogen administered in immunoeffective amounts to generate antisera to epitopes of OMP B1 specific for *M. catarrhalis.* In this embodiment, the clinical sample is assayed for the presence of the antigen, i.e., *M. catarrhalis* expressing OMP B1. This antisera specific for *M. catarrhalis* may be used by contacting the clinical sample, and detecting the presence of immunocomplexes formed between the antisera and antigen that is present in the clinical sample. Thus, a diagnostic kit would contain the antibody generated to OMP B1 epitopes; a means for facilitating contact between the clinical sample and the antibody; and a means for detecting the presence of immunocomplexes formed.

EXAMPLE 5

This Example illustrates methods and compounds which the use of B1 protein as an immunogen for vaccine formulations against disease caused by *M. catarrhalis* infection.

This embodiment of the present invention is to provide B1 protein, and/or peptides formed therefrom, to be used as immunogens in a prophylactic and/or therapeutic vaccine for active immunization to protect against or treat infections caused by *M. catarrhalis*. For vaccine development, the B1 protein comprising the immunogen may be purified from *M. catarrhalis*, or a recombinant organism genetically engineered to express B1 protein, using the methods according to the present invention. In either case, the immunogen is included as the relevant immunogenic material in the vaccine formulation, and in immunoeffective amounts, to induce an immune response. Many methods are known for the introduction of a vaccine formulation into the human or animal to be vaccinated. These include, but are not limited to, intradermal, intramuscular, intraperitoneal, intravenous, subcutaneous, ocular, intranasal, and oral administration. As known to those skilled in the art, the vaccine may further comprise a physiological carrier such as a pharmaceutically acceptable solution, polymer or liposomes; and an adjuvant, or a combination thereof.

Various adjuvants are used in conjunction with vaccine formulations. The adjuvants aid in attaining a more durable and higher level of immunity using smaller amounts of vaccine antigen or fewer doses than if the vaccine antigen were administered alone. The mechanism of adjuvant action is complex and not completely understood. However, it may involve immunomodulation through the stimulation of cytokine production, phagocytosis and other activities of the reticuloendothelial system, as well as delayed release and degradation/processing of the antigen to enhance immune recognition. Examples of adjuvants include incomplete Freund's adjuvant, Adjuvant 65 (containing peanut oil, mannide monooleate and aluminum monostearate), oil emulsions, glycolipid analogs, lipopeptides, Ribi adjuvant, the pluronic polyols, polyamines, Avridine, Quil A, saponin, MPL, QS-21, and mineral gels such as aluminum hydroxide, aluminum phosphate, etc.

Another embodiment of this mode of the invention involves peptides derived from B1 protein as a hapten, i.e. a molecule which cannot by itself elicit an immune response. In such case, the hapten may be covalently bound to a carrier or other immunogenic molecule which will confer immunogenicity to the coupled hapten when exposed to the immune system. Thus, such a B1-specific hapten liked to a carrier molecule may be the immunogen in a vaccine formulation. There are many such carriers known in the art including, but not limited to, keyhole limpet hemocyanin, bovine serum albumin, and diphtheria toxin cross-reactive mutant protein ("CRM"). Additionally, there are several methods known in the art for conjugating a peptide to a carrier. Such methods include, but are not limited to, the use of glutaraldehyde, or succinimidyl m-maleimidobenzoate, or 1-ethyl-3-(3-dimethyl-aminopropyl)carbodiimide, or the use of bromo-acetylated peptide (see, e.g. Robey et al., 1989, *Anal. Biochem.* 177:373–377).

In another embodiment, as an alternative to active immunization, such as where an immunocompromised individual is suffering from a potentially life-threatening infection caused by *M. catarrhalis*, immunization may be passive, i.e. immunization comprising administration of purified human immunoglobulin containing antibodies against the OMP B1. Alternatively, murine monoclonals, such as MAb 7B3 and/or MAb 1F11, can be modified for administration into such individual using techniques standard in the art (e.g., as reviewed by Adair, 1992, *Immunological Reviews* 130: 6–37, herein incorporated by reference). For example, murine monoclonal antibodies may be "humanized" by replacing portions of the murine monoclonal antibody with the equivalent human sequence. In one embodiment, a chimeric antibody is constructed. The construction of chimeric antibodies is now a straightforward procedure (Adair, 1992, supra, at p. 13) in which the chimeric antibody is made by joining the murine variable region to a human constant region. Additionally, chimeric antibodies may be made by joining the hypervariable regions of the murine monoclonal antibody to human constant regions and parts of human variable regions using one of several techniques known in the art. Techniques for constructing chimeric antibodies (murine-human) of therapeutic potential have been described previously (see, e.g., Morrison et al., 1984, *Proc. Natl. Acad. Sci.* 81:6851–6855; Larrick et al., 1991, *Hum. Antibod. Hybridomas* 2:172–189; herein incorporated by reference). Thus, in one embodiment of the present invention, and using methods known in the art, the murine variable region of the monoclonal antibody to B1 protein according to the present invention is joined to a human constant region to form a chimeric anti-B1 protein monoclonal antibody having the same specificity as the anti-B1 protein MAb. In general, humanizing an murine MAb such as by making a chimeric antibody limits the development of human anti-mouse antibody responses. Additionally, the humanized antibodies generally change the pharmacokinetics by providing a longer half-life of immunoconjugates containing such antibody, as compared to the half-life of immunoconjugates containing murine antibody.

A chimeric MAb can also be constructed using a standard combination of techniques including polymerase chain reaction (PCR) cloning of antibody variable regions, the use of suitable expression vectors already containing the DNA encoding human constant region, insertion of the DNA for the murine MAb variable region into such vector in forming a recombinant vector, and expression of the resultant chimeric antibody by an expression system containing the recombinant vector (See, e.g., Daugherty et al., 1991, *Nucl. Acids Res.* 19:2471–2476; Maeda et al., 1991, *Human Antibodies and Hybridomas* 2:124–134; herein incorporated by reference). One expression vector can be used in which the vector is constructed so that the variable region and constant region genes are in tandem. Alternatively, the DNA encoding the mouse variable region is inserted into one expression vector, and the DNA encoding the human constant region can be inserted into a second expression vector, followed by transfections using both the first and second expression vectors. Expression systems known to those skilled in the art for production of antibody or antibody fragments include mammalian cells (e.g. cell lines such as COS, NSO, or CHO), phage expression libraries, *Escherichia coli*, and yeast (Adair, 1992, supra).

These antibodies (purified human antibodies or purified, chimeric monoclonal antibodies) should have one or more of the functional properties including bactericidal activity thereby being a class of antibody that activates complement and which recognizes a surface-exposed epitope in vivo; or opsonic activity thereby being a class of antibody that interacts with immune clearing cells (e.g., macrophages) and which recognizes a surface-exposed epitope in vivo. In that regard, and as demonstrated in Example 3, in individuals infected with *M. catarrhalis* are elicited IgG antibodies that recognize a surface-exposed epitope of OMP B1 on *M. catarrhalis*.

It should be understood that while the invention has been described in detail herein, the examples were for illustrative purposes only. Other modifications of the embodiments of the present invention that are obvious to those skilled in the art of microbial pathogenesis, medical diagnostics, vaccines, and related disciplines are intended to be within the scope of the appended claims.

What is claimed is:

1. An isolated and purified outer membrane protein B1 of *Moraxella catarrhalis.*

2. The B1 protein of claim 1, wherein the protein is isolated from a bacterial strain comprising *Moraxella catarrhalis* grow in iron-limited conditions.

3. The B1 protein of claim 1, wherein the protein is further characterized by comprising a sequence of 9 amino acids consisting of SEQ ID NO:1.

4. An immunogenic composition, comprising an immunoeffective amount of an immunogen consisting of the outer membrane protein according to claim 1.

5. The immunogenic composition according to claim 4, further comprising a pharmaceutically acceptable carrier.

6. The immunogenic composition according to claim 5, wherein the pharmaceutically acceptable carrier is selected from the group consisting of a solution, a polymer, a liposome, an adjuvant, and a combination thereof.

7. The immunogenic composition according to claim 4 formulated for in vivo administration to an individual for inducing antibodies in the individual which are immunoreactive with B1 protein.

8. The immunogenic composition according to claim 5 formulated for in vivo administration to an individual for inducing antibodies in the individual which are immunoreactive with B1 protein.

9. The immunogenic composition according to claim 6 formulated for in vivo administration to an individual for inducing antibodies in the individual which are immunoreactive with B1 protein.

10. A diagnostic kit for the detection of *M. catarrhalis*-specific antibodies immunoreactive with outer membrane protein B1 of *M. catarrhalis* in a sample, said kit comprising:

(a) isolated and purified B1 protein as an antigen;

(b) a means for contacting the sample and the antigen; and (c) a means for detecting the presence of immunocomplexes formed between the antigen and any *M. catarrhalis*-specific antibodies immunoreactive with outer membrane protein B1 that may be present in the sample.

* * * * *

```
                    SEQUENCE LISTING

(1) GENERAL INFORMATION:

   (iii) NUMBER OF SEQUENCES: 1

(2) INFORMATION FOR SEQ ID NO:1:

     (i) SEQUENCE CHARACTERISTICS:
          (A) LENGTH: 9 amino acid residues
          (B) TYPE: amino acid
          (C) TOPOLOGY: linear

    (ii) MOLECULE TYPE:
          (A) DESCRIPTION: peptide

   (iii) ORIGINAL SOURCE: synthesized

    (iv) SEQUENCE DESCRIPTION: SEQ ID NO:1:

Leu Gln Gly Gly Phe Tyr Gly Pro Lys
  1               5
```